(12) United States Patent
Böhle et al.

(10) Patent No.: US 6,896,888 B1
(45) Date of Patent: May 24, 2005

(54) TREATMENT OF PAPILLOMA VIRUS INFECTION USING A MYCOBACTERIUM

(76) Inventors: Andreas Böhle, Fasanenring 2, D-23627 Gross Grönau (DE); Dieter Jocham, Zwinglistrasse 1, D-23568 Lübeck (DE)

(*) Notice: Subject to any disclaimer, the term of this patent is extended or adjusted under 35 U.S.C. 154(b) by 0 days.

(21) Appl. No.: 09/674,172

(22) PCT Filed: Apr. 29, 1999

(86) PCT No.: PCT/EP99/02930

§ 371 (c)(1),
(2), (4) Date: Jan. 4, 2001

(87) PCT Pub. No.: WO99/55347

PCT Pub. Date: Nov. 4, 1999

(51) Int. Cl.$^7$ ............................................. A61K 39/04
(52) U.S. Cl. .................... 424/248.1; 424/400; 424/405; 424/407; 424/489; 424/184.1; 424/234.1; 424/282.1; 424/83.1
(58) Field of Search ................................ 424/400, 405, 424/407, 489, 184.1, 234.1, 248.1, 282.1, 93.1

(56) References Cited

FOREIGN PATENT DOCUMENTS

GB          2179858 A   *   3/1987   ..........   A61K/31/70

OTHER PUBLICATIONS

Brandau et al., Urological Research (1997) vol. 25, No. 1, p. 94.*

Herr et al. (Journal of Urology vol. 141, pp. 22–29, 1989).*
Westenend et al., (BJU International (2001), 88,198–201).

* cited by examiner

Primary Examiner—L. F. Smith
Assistant Examiner—Robert A. Zeman
(74) Attorney, Agent, or Firm—Sim & McBurney

(57) ABSTRACT

Disease cased by papilloma virus is treated by applying an effective amount of *Mycobacterium* to the region of infection. Specifically, condylomata acuminata are caused by human papilloma virus infection. Despite numerous treatment modalities these patients often demonstrate recurrent disease. BCG therapy is used in primary treatment or in patients not responding to or recurrent after standard treatment. Six men with rapidly recurrent external and intraurethral condylomata acuminata underwent BCG therapy after initial laser treatment. External application and intraurethral instillation of BCG was performed six times in weekly intervals. Follow-up studies included examination and endoscopic inspection of the urethra and bladder. Three patients completed one course of BCG and had no relapse of condylomata acuminata. Two patients underwent a second course of BCG, of whom one relapsed. One patient relapsed after discontinued therapy due to penile edema. The annual recurrence rate decreased from 3.2 before the BCG therapy to 0.75 after BCG therapy (p<0.05, test of equality of 2 percentages). In addition, eight men underwent BCG therapy as primary therapy without initial laser treatment, following the same course of treatment, but employing BCG in a cream with salicylic acid to promote keratolysis. Six out of eight patients completely recovered. The BCG-induced immune response appears to reduce the recurrence rate in patients with condylomata acuminata.

14 Claims, No Drawings

TREATMENT OF PAPILLOMA VIRUS INFECTION USING A MYCOBACTERIUM

REFERENCE TO RELATED APPLICATIONS

This application is a national phase application under 35 U.S.C. 371 of PCT/EP99/02930.

FIELD OF INVENTION

The present invention relates to the treatment of disease caused by papilloma virus infection in humans, in particular to the treatment of condylomata acuminata caused by human papilloma virus in humans.

BACKGROUND OF THE INVENTION

Human papilloma virus (HPV) infections of the urogenital tract represent the most often sexually transmitted viral disease in humans (refs. 1 to 3-various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure). HPV is a double stranded DNA virus and with the recent developed molecular biological techniques, more than 55 different HPV types have been recognized (ref. 4). HPV is associated with a wide spectrum of clinical states including condylomata acuminata, latent and subclinical infection, and Bowen's disease. Subclinical infections gain more importance as they are believed to cause intraepithelial neoplasia, based on the frequent detection of HPV DNA in invasive carcinomas, especially in urogenital region (refs. 1, 5). A significant risk for the development of an invasive cancer is ascribed to the infections by HPV types 16, 18 and 33 (refs. 6 to 9).

The most prevalent HPV types causing condylomata acuminata are type 6 and 11. Condylomata acuminata are visible, multifocal, multicentric and multiform lesions. Predilection sites are penis, scrotum, perineum, urethra, perianal regions, intertriginous zones, and oral mucosa. In uncircumcised men the frenulum, the coronary sulcus and the inner aspect of the foreskin are most often afflicted, whereas in circumcised patients the shaft of the penis is involved. Genital warts are of great psychological and cosmetic relevance representing a major hindrance to sexual performance.

Treatment options include surgical methods like excision, electrocautery, cryosurgery or laser vaporization. It has been shown in molecular hybridization studies that HPV DNA sequences exist in adjacent normal tissue after carbon dioxide laser removal of genital warts (ref. 10). These findings and the well known high recurrence rates after initial treatment demonstrate the need for adjuvant therapy to eradicate invisible disease. Therapeutic results with local application of cytotoxic agents, for example, 5-fluorouracil and podophyllin/podophyllotoxin have, however, been unsatisfactory (refs. 11 to 13). Furthermore, several types of interferons (IFN) as well as autologous vaccines have been tried with varying success (refs. 2, 14 to 17). More recently, oral isotretionin has been given with some success to reduce the recurrence rate (refs. 18, 19, 20).

SUMMARY OF INVENTION

In accordance with one aspect of the present invention, there is provided a method of treatment of disease caused by papilloma virus, which comprises applying an effective amount of *Mycobacterium* to the region of infection.

In particular, the present invention in accordance with the treatment of infections caused by human papilloma virus (HPV) using the *Mycobacterium*. Such infection may include cutaneous and genital warts in humans, including verruca vulgaris and condyloma acuminatum, cervical intraepithelial neoplasia and genital carcinomas. In general, the treatment is applicable to any disease condition caused by HPV in humans including penile, intraurethral, perianal, intra-anal or perineal infections in men and cervical, vaginal, perigenital, intra-urethral, intra-anal and perineal infections in women, including condylomata acuminata, penile cancer, Bowen's disease, cervical cancer, head and neck cancer, laryngeal papiliomatosis and laryngeal carcinoma. The present invention is illustrated by application to recurrent external and intraurethral condylomata acuminata in men.

The *Mycobacterium* which may be employed may be an attenuated form of a *Mycobacterium* of the tuberculosis complex and, in particular, may be an attenuated form of *M. bovis*, specifically *Bacillus* Calmette-Guerin (BCG).

The treatment may be effected by application of the *Mycobacterium* in a suitable carrier to the region of infection, which may involve topical application to cutaneous, penile and perianal areas, or intraurethral application to the urogenital tract. The treatment also may be effected by inhalation, oral application or as an enema. The treatment may involve a single or a plurality of dos es applied at time intervals. The individual dosage level may be about 1 mg to about 500 mg while the time interval between doses may vary from about 1 to about 30 days. The number of treatments applied is from 1 to about 30 treatments. The treatment may be preceded by laser or other surgical or topical therapy.

The *Mycobacterium* may be formulated with a keratolytic agent for topical application to the region of infection, particularly as a cream for adherent application to the region of infection. The keratolytic agent may be salicylic acid, which may be powdered. The keratolytic agent may be present in an amount of about 0.1 to about 50 wt %, preferably about 1 to about 10 Wt %.

The composition which is applied to the area of infection may take any desired form, for example, a cream, a powder or ointment. Any desired form of application may be employed, including slow-release systems, plasters and transdermal systems.

The present invention further includes, in an additional aspect thereof, a therapeutic composition for the treatment of a disease condition caused by papilloma virus, comprising an effective amount of a *Mycobacterium* formulated with a keratolytic agent for topical application to a region of infection. Such composition may be formulated as described above.

The present invention extends, in a further aspect thereof, to the use of a *Mycobacterium* in the manufacture of a medicament for the treatment of infection caused by papilloma virus, particularly human papilloma virus.

GENERAL DESCRIPTION OF INVENTION

A wide spectrum of therapeutic approaches has been used over the past years for the management of condylomata acuminata. However, no form of therapy has yielded consistently effective results. In order to avoid recurrence of disease, the combination of surgical ablative methods and immunomodulative agents seem to be promising. Due to their antiviral, immunomodulative and antiproliferative properties, interferons have been given as a topical and systemic form of treatment for condylomata acuminata.

Interferons were also chosen for their mild side effect profile but recurrence rates up to 75% have been reported (refs. 2, 14 to 17).

In the case studies reported below, patients treated with BCG were cleared of warts and cytological evidence of HPV and had no recurrence of disease. One set of patients had previously experienced between two and five recurrences of condylomata acuminata. The annual recurrence rate was significantly reduced from 3.2 with standard therapy to 0.75 with BCG therapy. The incidence of side effects due to BCG therapy was low. One patient reported mild dysuria after the second and third BCG application of this first treatment course. Another patient had a penile edema and fever which was managed conservatively. Penile edema is a rare complication after intravesical BCG instillation. However, with intraurethral installation of BCG for transitional cell carcinoma of the urethra has been reported by Baniel et al (ref. 21). Serious complications like sepsis or hematuria were not observed in the reported group.

A second set of patients had no previous treatment for the condition and were given treatment with BCG without prior laser surgery. Complete disappearance of all visible condylomata acuminata was achieved in six out of eight patients and no relapse was reported. Incomplete regression was obtained in two cases. No side effects were reported.

EXAMPLES

The above disclosure generally describes the present invention. A more complete understanding can be obtained by reference to the following specific Example. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example contains the results of clinical trials in which BCG was used as adjuvant therapy to laser surgery.

Between October 1994 and March 1997, six men with rapidly recurrent external and intraurethral condylomata acuminata were selected for BCG therapy. The mean age was 27 years (range 22 to 32 years). All patients had previously undergone therapy for recurrent condylomata acuminata in other dermatological and urologic departments (see Table 1 below). The patients were informed they were undergoing an experimental treatment approach and all individuals gave written informed consent.

Examination of the penis and scrotum was performed without and with acetic acid application and lesions were treated with the neodymium:yttrium-aluminum-garnet (ND:YAG) laser (Dornier Medilas Fibertome 4060) at 10 to 20 W. Endoscopic inspection of the urethra and bladder was also performed and visible lesions treated with the Nd:YAG laser. Finally, the perianal region was inspected and laser treatment, when necessary, applied.

A minimum interval of 3 weeks between laser therapy and BCG application was utilized. For internal application of BCG, 81 mg of Connaught strain (Pasteur Mérieux Connaught Canada, North York, Ontario, Canada) were dissolved in 2 ml of sterile saline. The solution was directly instilled into the urethra with low pressure and kept for a minimum of 2 hours. To avoid preliminary emptying, a dressing was taped over the meatus. After 2 hours, the dressing was removed and the patient allowed to void spontaneously. A total of six BCG instillations were given at weekly intervals.

For external application, eighty-one mg of BCG Connaught strain were again dissolved in 2 ml of sterile saline. The solution was put onto a dressing which was gently wrapped around the sulcus and other affected areas. The dressing was fixed and kept for 2 hours as a moist chamber. This procedure was also repeated six times at weekly intervals.

The courses of six patients are given below and in Table 1 below:

Case 1

A 22-year-old male patient developed condylomata acuminata in 1994. Initially, the frenulum and the meatus were involved. He was treated with local podophyllin but relapsed twice, and was referred to the urological department in April 1995. Over a period of 13 months, five relapses occurred despite internal and external laser application. From July until October 1996, six intraurethral instillations and external applications of BCG were given in weekly intervals. At follow-up of 11 months, no relapse had been noticed.

Case 2

A 28-year-old male patient demonstrated with perianal and preputial condylomata in May 1995. Cystoscopy revealed additional lesions of the urethra and, therefore, internal and external laser therapy was performed. Three months later an urethral relapse was diagnosed and again treated with laser. Subsequently, the patient received six intraurethral instillations combined with external application of BCG. At follow-up of 29 months, no relapse had been noticed.

Case 3

A 26-year-old male patient had initial diagnosis of condylomata acuminata in 1992. The affected sites included the meatus and frenulum as well as the perianal region. Over a period of 15 months, four relapses occurred which were all managed with laser therapy. In September 1995, intraurethral instillation and external application of BCG was performed. At follow-up of 24 months, no relapse had been noticed.

Case 4

A 32-year-old man developed condylomata acuminata in February 1995. He had a hypospadia without operative correction required. Initial involvement included the meatus, subsequently frenulum and urethra had been involved. During the next 16 months, four relapses were diagnosed and treated with laser. Intraurethral BCG was given in August and September 1996. After 2 further relapses, intraurethral instillation and external application of BCG was repeated in January and February 1997. At follow-up of 8 months, no relapse had been noticed.

Case 5

A 31-year-old male had initial diagnosis of condylomata acuminata in January 1993. Primarily, meatus and foreskin were affected. In the next 27 months, four relapses occurred and managed with laser therapy. The first course of intraurethral instillation and external BCG application was performed in May and June 1995. The patient had three relapses which were treated with laser. In June and July 1996, he received a second course of BCG. He demonstrated one relapse which was lasercoagulated and at follow-up of 12 months, no further relapse had occurred.

Case 6

A 27-year-old male patient demonstrated condylomata acuminata in August 1996. Penis, meatus and urethra were involved. After two relapses, BCG was applied in July 1997. Due to side effects, the treatment was stopped after the third instillation. He had demonstrated a penile edema and fever (38.5° C.) and was treated with antiphlogistic drugs and ice packages. At follow-up of 3 months, one new penile lesiion had developed.

In summary of the clinical results obtained in this Example, three patients completed one course of BCG. These patients had no relapse in follow-up studies (Table 1). Two patients underwent a second course of BCG after recurrence of condylomata acuminata. One of them remained without relapse after the second course in a follow-up period of 8 months. The other patient had one relapse after the second BCG course. One patient developed a relapse after he had discontinued therapy due to side effects following the third BCG instillation of his first course.

With respect to side effects, one patient reported mild dysuria after the second and third BCG instillation of his first treatment course. Another patient was withdrawn from BCG therapy due to penile edema and fever. No other side effects were reported.

Before BCG therapy, 36 recurrences of condylomata acuminata were noted in 136 observation months compared to 6 episodes during 96 months after treatment. Therefore, the annual recurrence rate before BCG therapy was 3.2 and 0.75 thereafter. These results were statistically significant ($p<0.05$, test of equality of 2 percentages, (ref. 22).

Example 2

This Example contains the results of clinical trials in which BCG was used alone without prior laser surgery.

A group of eight men with primary external (n=6) and intraurethral (n=2) condylomata acuminata, who had no previous treatment for the condition, were treated by six applications or instillations of BCG, given at weekly intervals, following the protocol described in Example 1, but without any prior laser surgery.

The preparation employed was prepared as follows:

30 mg of salicylic acid powder plus 30 mg of an inert vehicle consisting of 0.5% silicon dioxide in D-mannitol was dissolved and suspended in 3 ml sterile (0.9%) saline.

81 mg of Connaught strain BCG then was added to form a paste or cream. The paste or cream adhered very well to the skin. After application or instillation a condom was applied for two hours and no further dressing applied.

In six of the eight cases, there was a disappearance of all visible condylomata acuminata, as determined both by external inspection and by the acetic acid test. No patient has yet reported a relapse.

In the other two cases, both with meatal condylomata, there was only incomplete regression and both patients received a second course of BCG treatment following Nd:YAG laser treatment.

No side effects were reported by any of the patients.

SUMMARY OF DISCLOSURE

In summary of this disclosure, BCG therapy is useful in treating condylomata acuminata, particularly rapidly recurrent conditions. In general, *Mycobacteria* are useful in treating infections caused by papilloma virus. Modifications are possible within the scope of this invention.

TABLE 1

| Patient # | AGE | No. previous occurences | No. relapses before BCG | No. relapses after BCG | Localisation of replases before BCG | Localisation of relapses after BCG |
|---|---|---|---|---|---|---|
| 1 | 22 | 3 | 5 | 0 | Urethra, frenulum, meatus | |
| 2 | 28 | 1 | 2 | 0 | foreskin, perianal | |
| 3 | 26 | 5 | 4 | 0 | frenulum, urethra, meatus | |
| 4 | 32 | 1 | 4 | 2, 0 after 2nd course | frenulum, urethra, urethra | frenulum, urethra |
| 5 | 27 | 3 | 4 | 3, 0 after 2nd course | foreskin, meatus urethra | foreskin, meatus urethra |
| 6 | 27 | 1 | 3 | 1 (incomplete course) | meatus, urethra | meatus, urethra |

REFERENCES

1. Syrjänen K. J.: HPV in genital squamous cell tumors: epidemiology and clinical synopsis. In, Genital *Papillomavirus* Infections. Edited by G. Gross, S. Jablonska, H. Pfister and H. E. Stegner. Berlin Heidelberg New York: Springer-Verlag, pp. 3–12, 1990.
2. Bonnez W., Oakes, D., Bailey-Farchione, A., Choi, A., Hallahan, D., Pappas, P., Holloway, M., Corey, L., Barnum, G., Dunne, A., Stoler, M. H., Demeter, L. M. and Reichman, R. C.: A randomized, double-blind, placebo-controlled trial of systemically administered interferon-α, -β, or -γ in combination with cryotherapy for the treatment of condyloma acuminatum. J. Infect. Dis., 171:1081, 1995.
3. Grin, W.: Condyloma acuminata-Epidemiologie und Therapie. Wien. Kin. Wochenschr., 104:215, 1992.
4. Barrasso, R., de Brux, J., Croissant, O. and Orth, G.: High prevalence of papillomavirus-associated penile intraepithelial neoplasia in sexual partners of women with cervical intraepithelial neoplasia. N. Engl. J. Med., 317: 916, 1987.
5. von Knebel Doeberitz, M. and zur Hausen, H.: Biological significance of human papillomavirus early gene expression in human cervical carcinoma cells. In: Genital *Papillomavirus* Infections. Edited by G,. Gross, S. Jablonska, H. Pfister and H. E. Stegner. Berlin Heidelberg New York: Springer-Verlag, pp.51–65, 1990.
6. Smith, K. T. and Campo, M. S.: Papillomaviruses and their involvement in oncogenesis. Biomed. Pharmacoth., 39: 405, 1985.
7. Pfister, H.: Biology and Biochemistry of Papillomaviruses. Rev. Physiol. Biochem. Pharmacol., 99: 111, 1984.
8. Syrjänen, S. M., von Krogh, G. and Syrjänen, K. J.: Detection of human papillomavirus DNA in anogenital condylomata in men using in situ DNA hybridisation applied to paraffin sections. Genitourin. Med., 63: 31, 1987.

9. Wiener, J. S., Effert, P. J., Humpphrey, P. A, Yu, L., Liu, E. T. and Walter, P. J.: Prevalence of human papilloma virus types 16 and 18 in squamous-cell carcinoma of the penis: a retrospective analysis of primary and metastatic sections by differential polymerase chain reaction. Int. J. Cancer, 50:694, 1992.

10. Ferenczy, A., Mitao, M., Nagai, N., Silverstein, S. J. and Crum, C. P.: Latent papillomavirus and recurrent genital warts. N. Engl. J. Med., 313: 784, 1986.

11. Swinehart, J. M., Sperling, M., Phillips, S., Kraus, S., Gordon, S., McCarty J. M., Webster G. F., Skinner, R., Korey, A. and Orenberg, E. K: Intralesional fluorouracil/ epinephrine injectable gel for treatment of condylomata acuminata. A phase 3 clinical study. Arch. Dermatol., 133: 67, 1997.

12. von Krogh, G., Szpak E., Andersson. M. and Bergelin, I.: Self-treatment using 0.25%–0.50% podophyllotoxin-ethanol solutions against penile condylomata acuminata: a placebo-controlled comparative study. Genitourin. Med., 70: 105, 1994.

13. Syed, T. A. and Lundin, S.: Topical treatment of penile condylomata acuminata with podophyllotoxin 0.3% solution, 0.3% cream and 0.15% cream. A comparative open study. Dermatology, 187: 30, 1993.

14. Davis, B. E. and Noble, M. J.: Initial experience with combined interferon-alpha 2 B and carbon dioxide laser for the treatment of condylomata acuminata. J. Urol., 147: 627, 1992.

15. Gross, G., Roussaki, A., Baur, S., Wiegand, M. and Mescheder, A.; Systemically administered interferon alfa-2a prevents recurrence of condylomata acuminata following CO2-laser ablation. The influence of the cyclic low-dose therapy regime. Results of a multicentre double-blind placeo-controlled clinical trial. Genitourin. Med., 72:71, 1996

16. Monsonego, J., Cessot, G., Ince, S. E., Galazka. A. R and Abdul-Ahad, A. K.: Randomisd double-blind trial of recombinant interferon-beta for condyloma acuminatum. Genitourin. Med., 72: 111, 1996.

17. Cardamakis, E., Kotoulas, I. G., Metalinos, K, Mantouvalos, H., Relakis, K, Scapari, M. Korantzis, and Papathanasiou, Z.: Treatment of urethral condylomata acuminata or flat condylomata with interferon-α2a. J. Vol. 152:2011, 1994.

18. Cardamakis, E. K. Kotoulas, I. G. B., Dimopoulos, D. P., Stathopoulos, E. N. Michopoulos, J. T. and Tzingounis, V. A: Comparative study of systemic interferon alfa-2a with oral isotretionin and oral isotretionin alone in the treatment of recurrent condylomata acuminata. Arch. Gynecol. Obstet., 258: 35, 1996.

19. Tsambaos, D., Geogiou, S., Monastini, A., Sakkis, T., Sagriotis, A. and Georz G.: Treatment of condylomata acuminattta with oral isotretionin. J. Urol, 158: 1810, 1997

20. Monk, B. J. and Burger, R. A.: New Therapies for Genital Condyloma in Women, Contemp OB/Gyn. 1998; Feb.: 81 to 96.

21. Baniel, J., Lev, Z., Engelstein, D. and Servadio, C.: Penile edema and meatal ulceration after intravesical instillation with *bacillus* Calmette-Guerin. Urology, 47: 932, 1996.

22. Sokal, R. R. and Rohif, F. J.: Test of equality of 2 percentages In: Biometry W. H. Freeman Company, San Francisco, p.p. 607 to 608, 1969.

What is claimed is:

1. A method of treatment of condylomata acuminata in humans, which comprises:

applying *Bacillus* Calmette-Guerin (BCG) to the affected area.

2. The method of claim 1 which comprises applying BCG to external and intraurethral condylomata acuminata.

3. The method of claim 1 which comprises applying BCG in about 1 to about 30 treatments to the affected area using an individual treatment dosage of from about 1 to about 500 mg of the BCG, wherein said applications are made at time intervals from about 1 to about 30 days where the applications number more than one.

4. The method of claim 1 which comprises performing ablative surgery to the affected area prior to said applying BCG.

5. The method of claim 4 wherein said ablative surgery is effected by laser.

6. The method of claim 1 which comprises formulating said BCG with a keratolytic agent for topical application to the affected area, and then topically applying said BCG to the affected area.

7. The method of claim 6 which comprises formulating BCG with a keratolytic agent for adherent application to the affected area, and then adherently applying said BCG to the affected area.

8. The method of claim 1 which comprises formulating said BCG with powdered salicylic acid as an adherent cream for application to the affected area, and then adherently applying said BCG to the affected area.

9. The method of claim 8 which comprises formulating said BCG with said salicylic acid in an amount of about 0.1 to about 50 wt % of the resulting formulation prior to said applying BCG to the affected area.

10. The method of claim 9 which comprises formulating said BCG said salicylic acid in an amount of about 1 to about 10 wt % of the resulting formulation prior to applying BCG to the affected area.

11. A therapeutic composition for the treatment of condylomata acuminate, comprising *Bacillus* Calmette-Guerin (BCG) formulated with a keratolytic agent for topical application to the affected area, wherein said keratolytic agent is powdered salicylic acid.

12. The composition of claim 11 wherein said salicylic acid is present in an amount of from about 0.1 to about 50 wt % of the composition.

13. The composition of claim 12 wherein said salicylic acid is present in an amount of about 1 to about 10 wt % of the composition.

14. A therapeutic composition for the treatment of condylomata acuminate, comprising *Bacillus* Calmette-Guerin (BCG) formulated with a keratolytic agent for topical application to the affected area, formulated with a keratolytic agent as a cream for topical adherent application to the affected area.

* * * * *